United States Patent [19]

Edmond et al.

[11] 4,152,929
[45] May 8, 1979

[54] ROOF BOLT TENSION DETERMINATION

[75] Inventors: Tibor O. Edmond; Kenneth C. Kestler, both of Ponca City, Okla.

[73] Assignee: Continental Oil Company, Ponca City, Okla.

[21] Appl. No.: 863,778

[22] Filed: Dec. 23, 1977

[51] Int. Cl.² .................... G01B 17/04; G01N 29/00
[52] U.S. Cl. ......................... 73/581; 73/761; 73/778
[58] Field of Search ............... 73/88 F, 579, 581, 584; 116/DIG. 34

[56] References Cited

U.S. PATENT DOCUMENTS

| | | | |
|---|---|---|---|
| 2,040,874 | 5/1936 | Pack | 73/DIG. 1 |
| 2,635,746 | 4/1953 | Gordon | 73/579 X |
| 3,097,523 | 7/1963 | Diamond et al. | 73/584 |
| 3,306,100 | 2/1967 | Wilhelm et al. | 73/581 |
| 3,960,009 | 6/1976 | Roepke et al. | 73/88 F |
| 4,062,229 | 12/1977 | Godfrey et al. | 73/88 F |

FOREIGN PATENT DOCUMENTS 1497834  9/1967  France .................................. 73/88 F

*Primary Examiner*—Charles A. Ruehl
*Attorney, Agent, or Firm*—Richard W. Collins

[57] ABSTRACT

Apparatus and method for determining the tensile load on a mine roof bolt, which is indicative of the support provided by the bolt. The device comprises a hammer for striking a roof bolt to produce a sound pulse, a microphone for picking up the sound pulse, and a sound comparator having a recorded sound or sounds whereby an operator can match the induced sound pulse with a recorded sound pulse to provide an indication of the tensile load on the roof bolt. The comparator may include a range of sounds, or may incorporate a variable speed function whereby the pitch of the recorded sound may be varied until the induced sound is matched. Comparison of the induced sound with the recorded sound provides an indication of the tensile load on the roof bolt.

5 Claims, 3 Drawing Figures

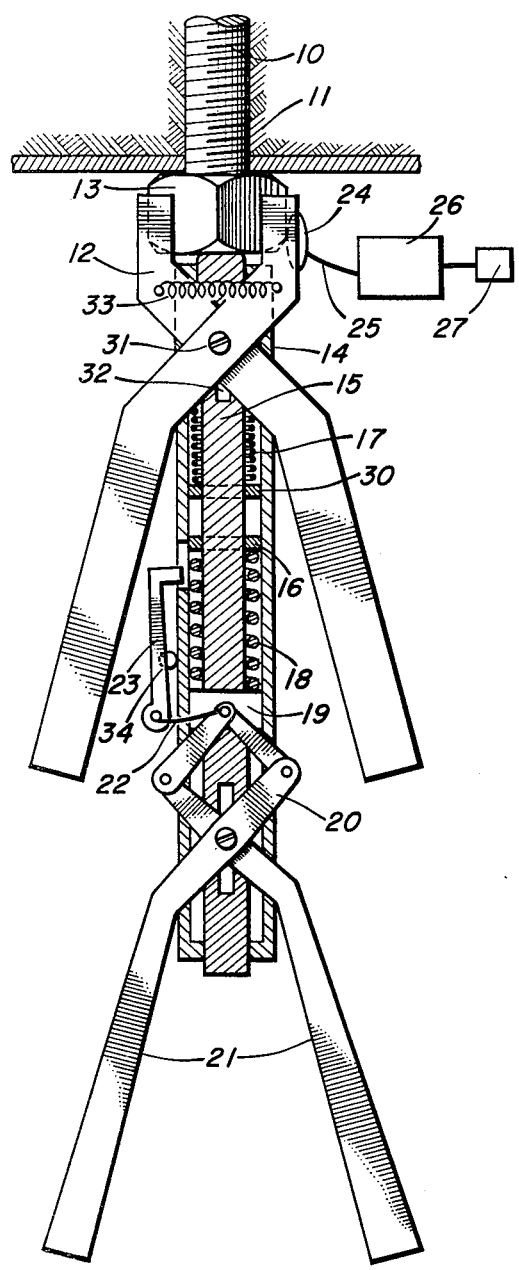
FIGURE I
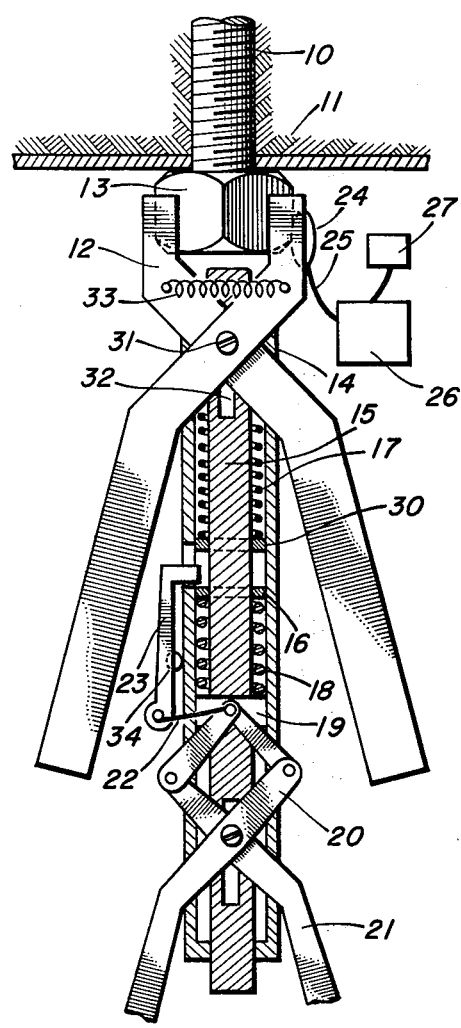
FIGURE II
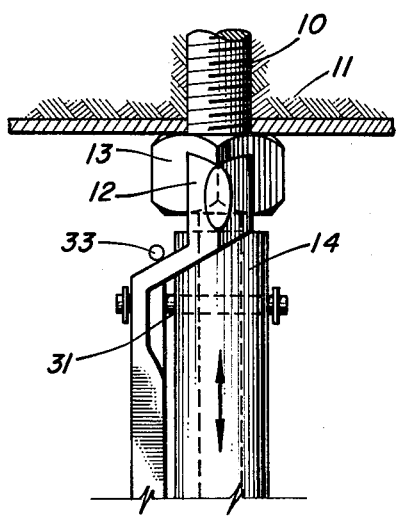
FIGURE III

ROOF BOLT TENSION DETERMINATION

BACKGROUND OF THE INVENTION

1. Field of the Invention

This invention relates to devices for indicating the tensile load of an elongated support member such as a mine roof bolt. The invention is applicable to determining the tensile load of elongated bolts in general, and is particularly useful for determining the tension in a mine roof bolt, and the following discussion is directed to the device and its use in connection with mine roof bolting.

It is common practice in the preparation of a mine tunnel for mining operations to support the formation of rock above the mine tunnel roof with a series of mine roof bolts. Conventional practice involves drilling small diameter holes in the mine roof and inserting long anchor bolts into these holes. The bolts generally have an expansible anchor means on the end which is inserted into the drilled hole. The bolt head is rotated, causing expansion of the anchor against the interior of the drilled hole. Another type of roof bolt utilizes a settable resin injected around the bolt. Support is provided by the tensile load imparted to the bolt upon tightening the bolt head into tight abutment with the mine roof, generally through a mounting plate positioned between the mine roof and the bolt head.

It is desirable to know approximately the support provided by a given bolt, both at the time of installation and afterwards during mining operations.

2. Description of the Prior Art

The problem of determining the degree of support provided by mine roof support bolts has been appreciated in the prior art, and numerous devices of varying degrees of reliability have been developed. A common approach has been to provide a tension indicating device affixed to the lower end of the bolt to indicate the stress imparted to the bolt. U.S. Pat. Nos. 3,131,468; 3,161,174 and 3,169,440 are representative of this type of attached bolt tension indicators. A more sophisticated device comprising a load cell attached to the lower end of a mine roof support bolt is described in U.S. Pat. No. 3,872,719.

Another approach to the measurement of bolt tension involves inducing a vibration in the bolt and measuring reflected vibrations from the bolt as an indication of the stress in the bolt member. U.S. Pat. Nos. 3,307,393 and 3,918,294, and French Pat. No. 1,497,834 are representative of this approach to the problem. Additionally, U.S. Pat. No. 3,097,523 describes a sonic testing device for detecting flaws in metal members such as castings. The device described therein includes a striking hammer for applying a predetermined blow to the casting, and includes a microphone pickup and electronics to analyze the induced sound. Analysis of the induced sound compared to known characteristics induced by similarly striking a known good casting provides an indication of the quality of the struck casting.

While each of the devices discussed above has been useful in solving the problem of determination of support provided by mine roof bolts and the like, there has nevertheless been a continuing need for an instrument which would enable an operator to reliably determine the support provided by a mine roof bolt both at the time of installation and after the bolt has been installed for a period of time. Desirable characteristics of such a device include reliability, portability, and simplicity. The present invention provides these characteristics in a manner not heretofore available.

SUMMARY OF THE INVENTION

According to the present invention, a device is provided having two essential components. These are a hammer for applying a blow to a bolt head, and a sound comparator for picking up the induced sound and reproducing it for comparison with a previously recorded sound indicative of a known tensile load. The hammer is integrally connected to a clamp for direct attachment to a bolt head, and the device can be carried and operated by a single operator.

The novel method in accordance with the invention comprises applying a blow of known force to a bolt head to produce a sound pulse, and comparing the induced sound pulse to a previously recorded sound or range of sounds to obtain a matching sound indicative of a particular tensile load in the bolt.

BRIEF DESCRIPTION OF THE DRAWINGS

FIGS. I and II are illustrations, partially cut away, showing a preferred version of the hammer and clamp portion of the device of the invention, FIG. I showing a hammer plunger in contact with a bolt head, and FIG. II showing the hammer plunger latched in position in a plunger barrel.

FIG. III is a view taken at a right angle to FIGS. I and II showing further details of the clamp portion.

DESCRIPTION OF THE PREFERRED EMBODIMENTS

In FIGS. I and II, a mine roof support bolt 10 is shown extending upwardly into an overlying mine roof formation 11. A clamp 12 is attached to the head 13 of roof bolt 10. Clamp 12 is affixed to a plunger barrel 14 which encompasses a plunger or hammer 15 movable longitudinally therein. Plunger 15 includes enlarged diameter sections 16 and 30, and is surrounded by a light return spring 17 above the enlarged section 30 and a heavy drive spring 18 below enlarged section 16. Drive spring 18 bears against compression ring 19 attached to a plunger actuator 20 through a linkage such that squeezing plunger actuator handles 21 will cause compression ring 19 to move upwardly relative to plunger 15 thereby compressing drive spring 18. When drive spring 18 is sufficiently compressed, linkage member 22 connecting plunger actuator 20 to releasable latch 23 causes latch 23 to rotate about pivot 34 and release enlarged section 16 of plunger 15 from the position shown in FIG. II whereby plunger 15 is propelled by drive spring 18 against bolt head 13 to the position shown in FIG. I. When plunger handles 21 are released, return spring 17 forces plunger 15 to the initial position where latch 23 again engages enlarged section 16, and the device is then ready for producing another blow against bolt head 13 if desired.

A microphone pickup 24 is attached to clamp 12, and is connected by lead 25 to sound comparator 26. Sound comparator 26 houses a recorded sound or range of sounds which can be produced automatically or on operator demand for comparison with the sound induced by the action of plunger 15 against bolt head 13. Sound comparator 26 conveniently includes controls for the volume of the induced sound and of the recorded sound, and in accordance with one embodiment includes means for varying the speed of the recording element, preferably a magnetic tape, to vary the pitch of the recorded sound. According to another embodiment of the invention, sound comparator 26 need not include the speed control for the recorded sound, in which case it is desirable to include a range of sounds on the recording element for comparison with the induced sound. In either of the above-discussed embodiments, the amount of tension in the bolt being tested can be determined by matching the induced sound with the sound produced by a similar action against a similar bolt under similar tension. Preferably, a set of head phones 27 are connected to sound comparator 26 to enable an operator to more precisely compare the induced and recorded sounds.

In FIG. III, clamp 12 is shown attached to barrel 14 by pin 31 extending through barrel 14 and slot 32 (FIGS. I and II) in plunger 15. Plunger actuator 20 is similarly attached to barrel 14.

Two preferred embodiments of the method in accordance with the invention will now be described with reference to the drawings. In the first embodiment in which the sound generated by striking the bolt head is compared to a series of prerecorded sounds, the procedure is as follows. Clamp 12 is attached to bolt head 13 and held in place by tension spring 33, and microphone 24 on clamp 12 is connected to sound comparator 26 through microphone lead 25. Sound comparator 26, in this embodiment, contains a continuous tape having a repeating sequence of a series of sound pulses representative of a series of tensions for the bolt being tested. An operator, preferably wearing a set of head phones 27 connected to comparator 26, squeezes plunger actuator handles 21 to compress drive spring 18 by the action of compression ring 19 moving upwardly relative to enlarged section 16 of plunger 15. Plunger 15 is initially held in place by latch 23. Upon travel of linkage member 22 to the point where latch 23 rotates about pivot 34, latch 23 is moved outwardly from the position shown in FIG. I and plunger 15 is released for upward movement relative to plunger barrel 14. Compressed drive spring 18 propels plunger 15 into roof bolt head 13 with a suitable force for generating a sound pulse. The operator hears the sound pulse through head phones 27, and then activates the recorded sounds in sound comparator 26 to identify the recorded sound nearest in pitch to the induced sound. The bolt head may be struck repeatedly to aid the operator in making this comparison. The recorded sound which is nearest in pitch to the induced sound enables the operator to determine the tensile load in the bolt being tested, as the series of recorded sounds are preferably obtained by striking a control bolt in the same manner with the control bolt under a series of known tensile loads.

In accordance with a second embodiment of the method of this invention, sound comparator 26 contains a single continuous recorded sound, and the comparator is equipped with a variable speed control for increasing or decreasing the speed of the tape containing the recorded sound. From empirical calibrations of the tape speed, the induced sound and the prerecorded sound can be matched, and the tensile load determined by an empirical scale of tape speed versus tensile load. Otherwise, the method according to this embodiment is essentially identical to the method according to the first embodiment described.

It will be appreciated that either embodiment of the method of this invention could be carried out using a device other than that described herein. For example, the microphone 24 is not essential to the methods described herein, as the operator could listen to the actual sound induced by striking the bolt head rather than listening to the reproduced induced sound. Also, the reference sounds need not necessarily be prerecorded, but could be generated by an suitable means capable of producing a sound or series of sounds of predetermined pitch. It will further be appreciated that numerous variations and modifications could be made to the equipment described and shown herein without departing from the true scope of this invention. For example, the latch 23 need not necessarily be released by movement of linkage member 22, but could be separately actuated by the operator. Further, numerous variations in the design of the clamp and plunger actuator will be apparent to those skilled in the art.

We claim:

1. Apparatus for determining the tensile load on an elongated bolt comprising:
   clamp means for attachment to a bolt head;
   microphone means associated with said clamp means;
   sound comparator means for receiving and reproducing sounds picked up by said microphone means, said sound comparator means also having capability for periodically producing sounds representative of the sound from striking the head of a bolt having a particular tensile load; and
   hammer means associated with said clamp means and adapted to strike a bolt head to which said clamp means is attached.

2. Apparatus as defined in claim 1 wherein said sound comparator comprises a variable speed closed loop tape player whereby sounds representative of a range of bolt tensile loads can be produced.

3. Apparatus as defined in claim 1 wherein said sound comparator includes a magnetic tape having a series of sounds representative of sounds produced by striking the head of a bolt under a series of tensile loads recorded thereon.

4. Apparatus as defined in claim 1 including a set of headphones associated with said sound comparator.

5. Apparatus as defined in claim 1 wherein said hammer means comprises a spring-actuated plunger having releasable latch means whereby upon release of said latch means said plunger is propelled into contact with a bolt head to which said clamp means is attached, thereby producing a sound representative of the tensile load of the bolt.

* * * * *